(12) United States Patent
Schäublin

(10) Patent No.: US 10,993,788 B2
(45) Date of Patent: May 4, 2021

(54) RETAINER, COMBINATION OF A PACKAGING AND A RETAINER, ADAPTER AND A RETAINER WITH A SUPPORT STRUCTURE FOR A SURGICAL DEVICE

(71) Applicant: CAMLOG Biotechnologies GmbH, Basel (CH)

(72) Inventor: Markus Schäublin, Diegten (CH)

(73) Assignee: CAMLOG Biotechnologies GmbH, Basel (CH)

( * ) Notice: Subject to any disclaimer, the term of this patent is extended or adjusted under 35 U.S.C. 154(b) by 167 days.

(21) Appl. No.: 16/304,709

(22) PCT Filed: May 26, 2017

(86) PCT No.: PCT/EP2017/062761
§ 371 (c)(1),
(2) Date: Nov. 27, 2018

(87) PCT Pub. No.: WO2017/207434
PCT Pub. Date: Dec. 7, 2017

(65) Prior Publication Data
US 2019/0151053 A1 May 23, 2019

(30) Foreign Application Priority Data

Jun. 2, 2016 (WO) .................. PCT/EP2016/062568
Sep. 29, 2016 (EP) ..................................... 16191320

(51) Int. Cl.
*A61C 8/00* (2006.01)
*A61C 19/02* (2006.01)
(Continued)

(52) U.S. Cl.
CPC ............ *A61C 8/0087* (2013.01); *A61B 50/20* (2016.02); *A61B 50/30* (2016.02); *A61C 8/0089* (2013.01); *A61C 19/02* (2013.01); *A61C 3/00* (2013.01)

(58) Field of Classification Search
CPC ....... A61C 8/0087; A61C 8/0089; A61C 3/00; A61C 19/02; A61B 50/30; A61B 50/20
(Continued)

(56) References Cited

U.S. PATENT DOCUMENTS 6,086,371 A * 7/2000 Bassett ................ A61C 8/0087
206/339
6,164,442 A * 12/2000 Stravitz .................... A45C 3/02
206/233
(Continued)

FOREIGN PATENT DOCUMENTS

EP         1 087 719 B1      4/2001
KR       20-0448457 Y1      4/2010

OTHER PUBLICATIONS

International Search Report Corresponding to PCT/EP2017/062761 dated Dec. 14, 2017.
(Continued)

*Primary Examiner* — Steven A. Reynolds
(74) *Attorney, Agent, or Firm* — Davis & Bujold PLLC; Michael J. Bujold

(57) ABSTRACT

A retainer for holding at least a first surgical device, preferably a dental implant, and a second surgical device, preferably a healing screw, including a first body part and a second body part. The first and second body parts are pivotable relative to each other, and the first body part includes a first support structure for holding the first surgical device and the retainer includes at least one secondary support structure for the second surgical device. The first and the second body parts are pivotable in relation to each other to at least three predefined positions. In a first position, the first and second surgical devices are locked in the retainer; in a second position, the first surgical device is removable from the support structure, but not the second surgical device; and in a third position, the second surgical device is removable from the retainer.

22 Claims, 16 Drawing Sheets

Figure 1:
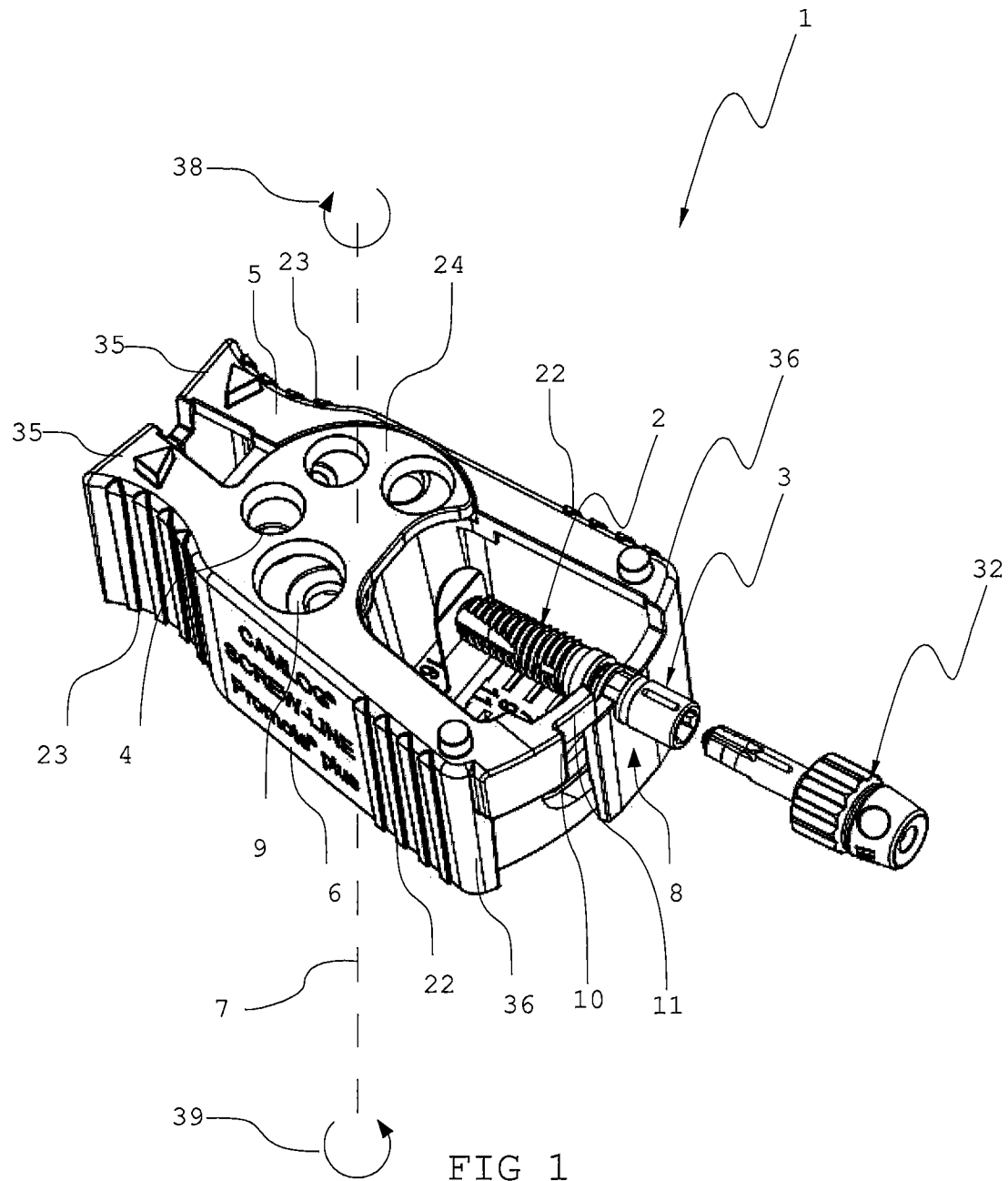

(51) Int. Cl.
    *A61B 50/30*     (2016.01)
    *A61B 50/20*     (2016.01)
    *A61C 3/00*     (2006.01)

(58) Field of Classification Search
    USPC .............................................. 206/63.5, 438
    See application file for complete search history.

(56) References Cited

U.S. PATENT DOCUMENTS

| | | |
|---|---|---|
| 8,292,075 B2 | 10/2012 | Liao et al. |
| 8,342,841 B2 * | 1/2013 | Vogel .................... A61C 19/02 |
| | | 433/77 |
| 8,973,747 B2 | 3/2015 | Schlottig et al. |
| 9,119,688 B2 | 9/2015 | Kenk et al. |
| 2007/0181446 A1 * | 8/2007 | Donahoe ................ A61B 50/30 |
| | | 206/63.5 |

OTHER PUBLICATIONS

Written Opinion Corresponding to PCT/EP2017/062761 dated Dec. 14, 2017.

\* cited by examiner

RETAINER, COMBINATION OF A PACKAGING AND A RETAINER, ADAPTER AND A RETAINER WITH A SUPPORT STRUCTURE FOR A SURGICAL DEVICE

The present invention relates to a retainer for holding at least a first surgical device and a second surgical device, and to a combination of a packaging for a retainer and a retainer according to the preamble of the independent claims. Further, the present invention relates to an adapter for a surgical device and a retainer comprising a support structure.

In dentistry, teeth may be artificially replaced by a dental implant, an abutment and a crown. In an implantation procedure first a jaw bone is accessed by incising an overlying gingival tissue. Then a position for the implant is identified. Into this position a drill drills a hole into the jaw bone. The dental implant is then implanted into this hole. After the implantation a dentist inserts a healing screw or a healing abutment into the dental implant and may close the surgical site for healing. At a later stage the site is reopened in a second operation and the healing screw is exchanged with an abutment. Lastly, a crown is placed onto the abutment to complete the operation. In some instances all steps may be executed in a single operation.

The coupling of the dental implant to the bone requires a suitable surface for osseointegration with the implant. Further, the implant is a medical device. It needs to be transported sterilely in a retainer. The retainer holds and protects the dental implant whilst the implant is transported and handled. During the implantation procedure the implant needs to be removed from the retainer. The implantation procedure may be facilitated by using an adapter which connects the dental implant to an insertion device.

U.S. Pat. No. 8,973,747 B2 provides a package for a dental implant which comprises a housing with a compartment that can be closed by way of a perforable or slidable cover. The compartment is essentially liquid tight. Further the package includes an opening for a healing cap. However, the procedure of removing the dental implant and the healing cap is not based on the needs of a surgeon or a surgical procedure. Hence the handling is complex. Further for liquid tightness expensive high precision fabrication techniques are required.

U.S. Pat. No. 9,119,688 B2 discloses a holding device for retaining and transporting a dental implant. The holding device comprises an engagement section for engaging a manipulating section, a retention section for retention on a packaging and a securing section for connection to a dental implant. The retention section includes annular shoulders and a circumferential groove defined by the annular shoulders. This groove functions to receive a mating structure such as a flange of an external package to allow a dental implant to be positioned within the package. However, there remains need for improvement of the removal procedure of the holding device from the package.

U.S. Pat. No. 8,292,075 B2 discloses a housing for accommodating a dental implant. The housing comprises a first body portion and a second body portion. In between those portions an inner space is defined. The second body portion is capable of rotating with respect to the first body portion along a pivot axis to expose an open end. This open end accommodates the dental implant. However, the device does not support a second surgical device such as a healing screw which is also needed during the implantation procedure. Additionally the housing forms an airtight space which increases fabrication costs.

The object of the present invention is to overcome disadvantages of the prior art. In particular the object of the invention is to provide an easy to use retainer which supports a surgeon during the procedure. Another object of the invention is to provide an affordable packaging for a retainer.

Another object of the invention is to provide an adapter which allows an easy removal of the dental implant from a retainer.

Another object of the invention is to provide a retainer with a support structure such that a surgical device is easily removable.

According to the invention the problem is solved with a retainer for holding at least a first surgical device and a second surgical device, a combination of a packaging for a retainer and a retainer, an adapter for a surgical device and a retainer with a holding structure according to the characterizing portion of the independent claims.

According to the invention a retainer for holding at least a first surgical device is provided. The first surgical device is preferably a dental implant or an adapter for a dental implant or a combination of an adapter and a dental implant. Further the retainer is also adapted for holding a second surgical device which is preferably a healing screw. The retainer comprises a first and a second body part. The first and the second body part are pivotable relative to each other. In a preferred embodiment they are pivotable around a pivot axis. The first body part includes a first support structure for holding the first surgical device and the retainer includes at least one secondary support structure for the second surgical device. The retainer is characterized by the first and the second body part of the retainer being pivotable in relation to each other to at least three predefined positions. In a first position the first and second surgical device are locked in the retainer. In a second position the first surgical device is removable from the support structure, but not the second surgical device. In a third position the second surgical device is removable from the retainer.

The first surgical device may be a dental implant. A dental implant is understood as a surgical component adapted to provide an interface with a bone of the jaw to support a dental prosthesis such as a crown, a bridge, or hybrid dentures.

The first surgical device may be a dental implant directly attached to the retainer. In a particularly preferred embodiment the first surgical device may also be a combination of a dental implant with an adapter wherein the adapter is directly connected to the retainer and holds the first surgical device.

The retainer may be made from a polymer, such as a polycarbonate, PET or PBT or any other suitable material.

The term "pivotable relative to each other" refers to at least one of the body parts having a pivoting motion. E.g. the first body part moves with relation to the second body part or vice versa or both body parts move. Preferably, the pivoting motion is around a fixed pivot axis. In alternative embodiments the pivot axis is not fixed in a particular location but may be variable.

The second surgical device may be a device which may aid during or after the implantation procedure. In particular, a second surgical device may be a healing screw which prevents ingrowth of tissue, in particular gingival tissue, into the implant.

The first position is a position preferably used for handling and transport because both surgical devices are firmly attached to the retainer.

As soon as a dentist needs the first surgical device the retainer may be brought into the second position and the first surgical device becomes removable. At this stage, only the first surgical device is needed. Thus, during removal of the first surgical device, the second surgical device should not be removable. If, at a later stage, the retainer is pivoted to the third position, the second surgical device can be removed from the retainer.

One advantage of the retainer is that it provides a holding structure for a second surgical device. Another advantage is an easy and convenient mechanism of removal by a pivoting motion.

Another advantage is that the retainer is adapted to the surgery procedure, i.e. the removal of devices is based on a surgical procedure as normally conducted. During the procedure first a first surgical device is needed and later the second surgical device. Surgical devices not yet needed may thus not be lost and remain fixed.

In a preferred embodiment the retainer includes a limiting portion which prevents movement to the third position. The limiting portion is preferably adapted to be unlocked by removing the first surgical device.

Thereby, the second surgical device cannot be removed unintendedly. Only after the limiting portion is unlocked, the second surgical device may be removed. In the preferred embodiment the first surgical device must be removed before the second surgical device. Thus, a second surgical device cannot be lost during surgery before needed.

The limiting portion is particularly preferred a portion of the second body part. The limiting portion may be designed such that the first surgical device limits the pivoting movement. In this case the first surgical device acts as a stopper.

In a preferred embodiment the retainer comprises a pivot axis which extends substantially perpendicular to a longitudinal direction of the first and second body parts.

The longitudinal direction is understood as the direction that extends along a longest dimension of the body part. Substantially perpendicular is understood as including perpendicular and an angle of plus or minus 20° to the perpendicular direction.

Thereby, the pivoting motion is actuated in a particularly simple manner. A lever effect used to actuate the body parts may be higher because a distance between pivot axis and a point where a force for pivoting first and second body part is applied may be higher.

In a preferred embodiment the retainer is pivotable from the first to the second position in a first direction and from the second to a third position in a second direction opposite to the first direction.

Direction is understood as a direction of a pivoting motion i.e. a rotation around an axis. Thereby, a risk of bringing the first and second body part accidentally in the third position is reduced.

In an alternative preferred embodiment the retainer is pivotable from the first to the second position in a first direction and from a second to the third position in the same first direction.

Thereby, the retainer may only comprise one means for actuating the body parts. This means can be used for both, bringing the first and second body part in the second position and for bringing the first and second body part into the third position.

In a preferred embodiment the retainer comprises first locking means. The first locking means prohibit the removal of the first surgical device, wherein the first locking means are preferably arranged in a second body part. Particularly preferred the first locking means are formed by a bar which closes the first support structure.

The first locking means provide security that the first surgical device may not be accidentally removed from the retainer. If the locking means are arranged on the second body part, then they may be unlocked with the pivoting motion.

In a preferred embodiment the retainer comprises second locking means for prohibiting the removal of the second surgical device. These second locking means are preferably arranged in the second body part. In one embodiment the second locking means are formed by a plate.

Thereby, the second surgical device may not be accidentally removed from the retainer while the first and second body parts are in either the first or second position. If the second locking means are arranged on the second body part and the second surgical device is held by the first body part, then they may be unlocked with the pivoting motion.

In a preferred embodiment the retainer comprises at least two secondary support structures for the second surgical device.

Thereby, one retainer can be used for alternating sizes of second surgical devices. For example the same retainer could comprise either a larger second surgical device or a smaller second surgical device. Alternatively the retainer may also hold two or more secondary surgical devices such that a surgeon may chose the suitable second surgical device.

In a particularly preferred embodiment each of the at least two secondary support structures is sized to receive a second surgical device with a corresponding size.

In a preferred embodiment the first surgical device is an adapter and a dental implant, wherein the adapter is preferably directly anchored to the retainer.

The adapter allows the use of a single insertion device for all sizes of dental implants. Hence, the retainer and its first support structure do not need to be adjusted for each individual dental implant size.

If the adapter is directly anchored to the retainer, the dental implant is only indirectly anchored to the retainer and requires no attachment structures for connection to the retainer. Further, an outer surface of a dental implant is not in direct contact with the retainer, and hence not damaged or polluted by the retainer. Also no structures or features are necessary for a direct connection to the retainer. Furthermore, a variety of materials may be used for the retainer which are otherwise unavailable due to the sensitive osseointegration surfaces of the implant.

In another preferred embodiment the first and second body part are made from at least one plastic material. In a particularly preferred embodiment each body part is made integrally.

Hence, the retainer may be fabricated cost-effectively due to lower material costs. If one or both of the body parts are made integrally then the advantage arises that the retainer may be fabricated cost-effectively in large numbers, e.g. by injection molding.

Preferably the body parts are producible by molding, preferably by injection molding or particularly preferably by two or more component injection molding. The two body parts are typically assembled by clipping or snapping the parts together.

Molding, in particular injection molding, is a cost-effective manufacturing technique for large volumes.

In a preferred embodiment the retainer additionally includes a stabilizing structure. The stabilizing structure comprises a contact section for contact with the first surgical device. In a particularly preferred embodiment the contact section is in contact with a distal end of the first surgical device. The distal end is the end which is implanted into the bone.

The stabilizing structure improves the fixation of the first surgical device to the retainer. It also may reduce the risk of losing or loosening the fixation of the first surgical device to the retainer.

In a preferred embodiment the contact section of the stabilizing structure consists of a metal, preferably titanium, niobium, tantalum, zirconium, or their alloys, or a ceramic, preferably zirconia.

Metals, in particular titanium, niobium, tantalum, zirconium, or their alloys, or ceramics, in particular zirconia are particularly suited for contact with the delicate surfaces which are adapted for bone adhesion. These surfaces are typically roughened and metal, in particular the above mentioned materials, reduce the risk of remnants attaching to these surfaces and being implanted such as with plastic materials.

In one embodiment the stabilizing structure may consist of one of the materials. In another embodiment the stabilizing structure may be a platelet onto which plastic parts are molded for fixation to the retainer. Also the stabilizing structure may be pluggable to the retainer. Alternatively the retainer and the stabilizing structure may be manufactured from one material.

In another preferred embodiment the retainer comprises at least two holding structures for the stabilizing structure. The stabilizing structure is attachable to any one of the at least two holding structures. Further, each holding structure may correspond to one size of the first surgical device.

Thereby, one retainer may be used for a plurality of sizes of first surgical devices, e.g. dental implants. The stabilizing structure is introduced into one of the holding structures according to the size of the first surgical device.

In a preferred embodiment the retainer comprises a labelling for the at least two holding structures indicating the corresponding size of the first surgical device.

Hence a user may be informed about the size of the dental implant held by the retainer.

In a preferred embodiment the retainer comprises engagement means for defining at least one of the positions, particularly preferred for defining the first, second and third position.

Thereby, during operation a position may be easily found and retained.

In a particular preferred embodiment the engagement means comprise a spring element with a ledge and multiple depressions for the ledge. Each depression may then define one position. If the ledge catches one position it also may retain this position.

In a preferred embodiment the retainer includes at least one projection for support on a flat surface.

This at least one projection may allow a stable stand of the retainer.

According to another aspect of the invention a combination of a packaging for a retainer and a retainer is provided. The packaging comprises a retainer receiving recess and a removable cover. The retainer comprises a first and a second body part. The first and the second body part are pivotable relative to each other to at least first and a second position. In the first position a surgical device is locked in the retainer and in the second position the surgical device is removable from the retainer. The packaging is formed such that a pivoting motion of the first and/or second body part is prohibited by contact between the retainer and the packaging.

Packaging is herein understood as a device to enclose and protect the retainer at least during transportation, storage, and/or handling.

One advantage is that the packaging can prohibit an unintended release of the surgical device from the retainer. Another advantage is that the packaging may keep the implant sterile during transportation, storage, and/or handling. In one embodiment the packaging may allow a sterilization of packaging and retainer. Particularly preferred the packaging includes a removable cover such that the retainer is easily accessible.

In a preferred embodiment the packaging is deformable such that the retainer can be held inside the recess by gripping an outer surface of the packaging. In a particularly preferred embodiment the packaging is elastically deformable.

Thereby, the retainer may be manually held in the packaging. This would allow an assistant to pass the retainer in a sterile manner i.e. without touching it with the fingers, to a dentist or the sterile tray.

The retainer may be offered by holding the retainer in the packaging by gripping the outer surface of the packaging and turning the packaging upside down. Then the retainer is placed on a sterile tray and the grip may be released. Afterwards the packaging is removed in a controlled fashion. Hence, the deformable packaging facilitates a sterile handling of the retainer.

In a preferred embodiment the first and second body part are pivotable around the pivot axis, wherein the pivot axis is substantially perpendicular to the longitudinal directions of the first and second body parts.

This is a particularly convenient and easy way to operate the retainer.

According to a preferred embodiment the packaging is a blister.

Blisters may offer low cost and/or customization to the size of the retainer. The blister may allow a user to see the retainer and surgical devices prior to use.

In a preferred embodiment the recess includes a free space between a wall of the recess and the retainer. This allows a gripping of the retainer by finger.

Thereby, the retainer may be directly removed from the packaging. Particularly preferred, the free space is defined by a protrusion in the wall of the recess. The protrusion may have a round or circular shape.

In a preferred embodiment the packaging includes a bulge for prohibiting a pivoting motion of a first and second body part. The bulge extends in between the two body parts of the retainer.

Thereby a pivoting motion of the first and second body part is prohibited.

According to a preferred embodiment a contact between the retainer and packaging is between an outer surface of the retainer and an inner surface of the packaging.

In a preferred embodiment the combination is sterilisable.

Hence, the packaging can be used to sterilely transport and handle the retainer. Non-limiting examples of methods for sterilization are irradiation, particularly irradiation with gamma rays or ethylene gas sterilization. The packaging may form a sterile barrier around the retainer. The packaging may fully enclose the retainer.

Packaging and retainer may be sterilisable in an assembled state.

The blister may be made from a polymer which is flexible. The blister may be made from a polymer, preferably a thermoplastic polymer, which is flexible. Examples of such polymers are PETG, PET, PBT, Polyolefins, COC or combinations thereof.

In a preferred embodiment the packaging forms a sterile barrier.

Thereby, the retainer may be transported, stored and handled in a sterile manner.

According to another aspect of the invention an adapter comprising a first end, a second end and a longitudinal axis is presented. The adapter comprises a surgical section provided at the second end for connection to a surgical device. The adapter also comprises an engagement section which is provided at the first end and which is adapted to engage an insertion device. Further, the adapter comprises a support section for connection to a retainer. The surgical section is on the side of the first end and comprises force or torque transmission means for the surgical device. On the first end an attachment element for a removable connection to the implant is placed. The support section comprises an at least partially non-circular shape such that the adapter is removable by rotating the adapter around its longitudinal axis.

The adapter may be made of a metal or a metal alloy or any combination of metals and/or metal alloys.

The force transmission means may be a spline shaft or a polygonal cross-section or a key seat with a key.

Thereby, a storage is enabled which allows a fast and easy removal of the adapter from a retainer. Also the adapter may be removed with an insertion device by attaching the insertion device to the adapter and rotating the adapter around its axis.

In a preferred embodiment the non-circular shape of the support section has a polygonal cross-section. In a particularly preferred embodiment the cross-section is hexagonal.

Hence, the adapter may easily removable from a support section with a corresponding shape. The angles of the polygonal cross-section may be round, such that handling is facilitated.

In another preferred embodiment the support section is arranged in a recess formed on the outer surface of the adapter.

Thereby, a stable fixation of the adapter in a retainer is enabled.

In a particularly preferred embodiment the attachment element for the connection to the implant comprises at least two, preferably at least three, particularly preferred exactly three, spring elements.

Thereby, the adapter may be releasably fixed to the surgical device. The spring elements provide a preset retention force which must be overcome to remove the adapter from the surgical device.

According to a preferred embodiment the at least two spring elements each comprise at least one pre-defined contact section for contact with the surgical device.

Hence, a retention force can be transmitted from the implant to the adapter. In some cases a surface to which the spring element is attached may comprise a threading. In those cases a distance between two or more contact sections may be adjusted to the pitch of the threading, i.e. be a multiple of the pitch.

In a preferred embodiment the at least one contact section has a cross section with a round shape along a longitudinal axis of the adapter.

Thereby, removing the adapter from the surgical device may be easier, i.e. the retention force may be lower.

According to a preferred embodiment the adapter comprises a predefined breaking point between the engagement section and the support section.

Thereby, a limitation element for the torque transmission is included in the device and damage to the implant is avoided.

According to another preferred embodiment the force or torque transmission means include a spline shaft.

A spline shaft is particularly suited to transmit rotational forces. A spline shaft is understood as a shaft having a number of preferably equally spaced grooves cut in the shaft so as to form a series of projecting keys and fitting into an internally grooved cylindrical member, called spline hub.

In another preferred embodiment the adapter comprises at least one marking on the side of the first end. The circumferential position of the marking may correspond to a circumferential position of at least one load of the spline shaft. In a particularly preferred embodiment the marking is an elongated notch or projection. The elongated notch or projection preferably extends along the longitudinal axis of the adapter.

Thereby, the rotational position of the adapter is indicated to a user. The adapter may hence be connected more easily, especially if the insertion device and/or the implant have similar markings.

In a preferred embodiment the engagement section is a spline hub.

A spline hub is understood as a hub having a number of preferably equally spaced grooves cut in an outer perimeter of the hub. Thereby, rotational forces may be transmitted particularly effectively.

In a preferred embodiment the adapter is formed to include a cavity in a cross-section of the force or torque transmission means. The cavity extends along the longitudinal axis.

In particularly preferred embodiments the cavity extends from the first end. Further preferred the cavity extends over at least ¼, particularly preferred ½, of the length of the force or torque transmission means.

As a result the cross-section of the force or torque transmission means has a lower area moment of inertia. The force or torque transmission means are more deformable and may twist easier. Hence, the force or torque transmission means adapt better to a counter contour of an implant. Thus, the force is transmitted more uniformly and possibility of damages on the implant are reduced.

According to another aspect of the invention a retainer for holding a surgical device is provided. The retainer comprises a support structure which is adapted to hold the surgical device at its support. The support structure has an at least partially non circular shape.

The support structure may allow a particularly easy removal of a surgical device from the retainer.

According to a preferred embodiment the support section partially envelops the surgical device.

Thereby, the surgical device is secured to the retainer.

In a preferred embodiment the non-circular shape of the support structure is V-shaped for receiving a hexagonal cross-section.

Thereby, if a supported hexagonal device is rotated, then the supported device is forced out of the recess.

In a preferred embodiment the support structure comprises projections for removably fixing the surgical device.

The projections provide a releasable fixation to the surgical device. Particularly preferred the projections are ledges.

Thereby, the surgical structure can be securely fixed the surgical device.

In a preferred embodiment the support structure comprises a gap for flexibly expanding at least a part of the support structure, particularly preferred for expanding an opening for inserting the surgical device.

Thereby, the support structure may be dimensioned such that it can expand while receiving the surgical device and compress when the surgical device is held. Thereby, a retaining force is increased. The support structure may comprise an elastically deformable material.

In a preferred embodiment the retainer comprises a first and a second body part. The first and the second body part are pivotable relative to each other. The support structure further comprises a limiting stop for a pivoting motion of either of the body parts. Particularly preferred, the first and second body part are pivotable relative to each other around pivot axis.

Thereby, a working area is set and the first and second body parts may not be pivoted outside of this working area in one direction of movement.

Figure 2:
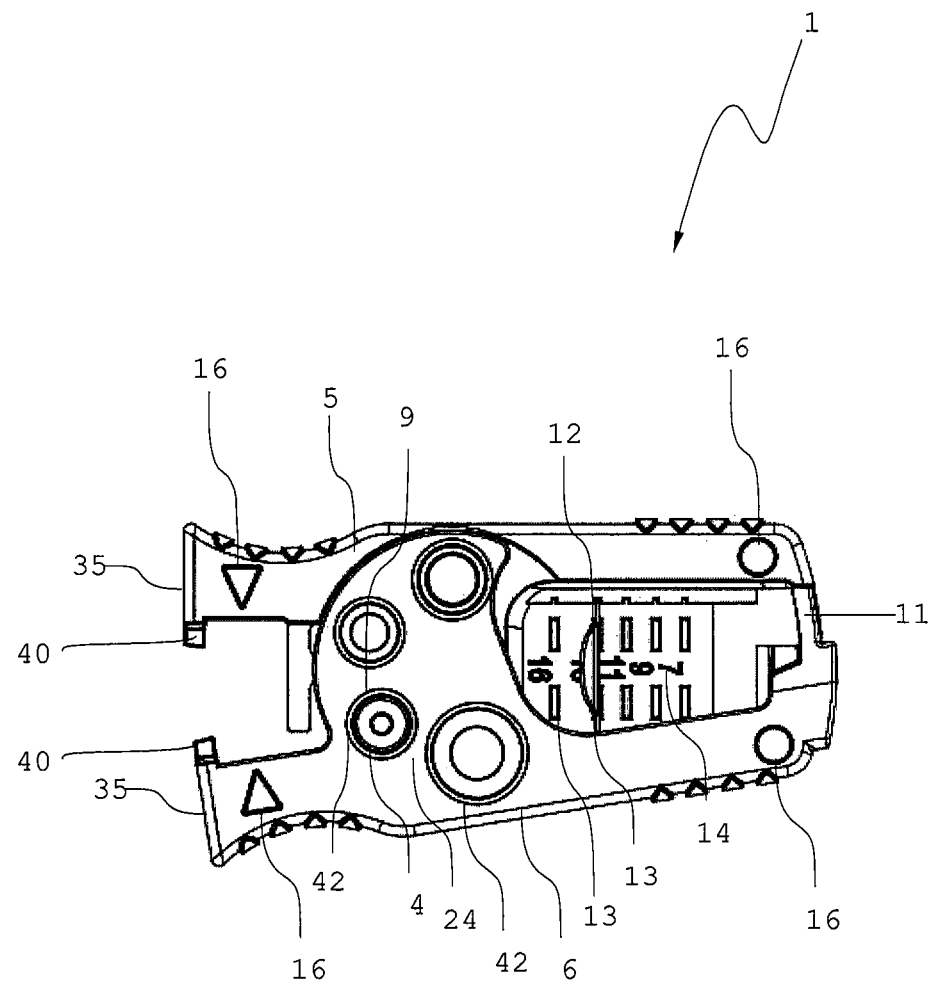
Figure 3:
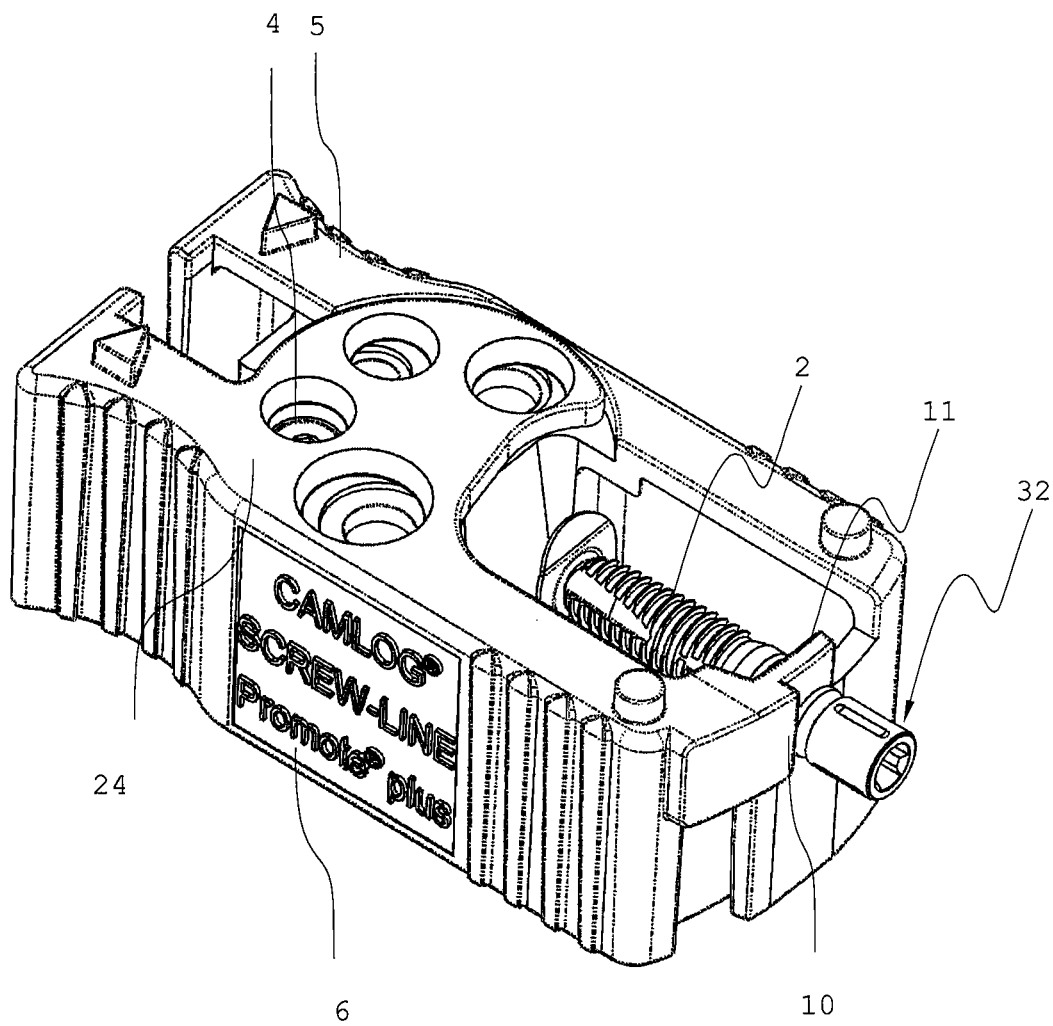
Figure 4:
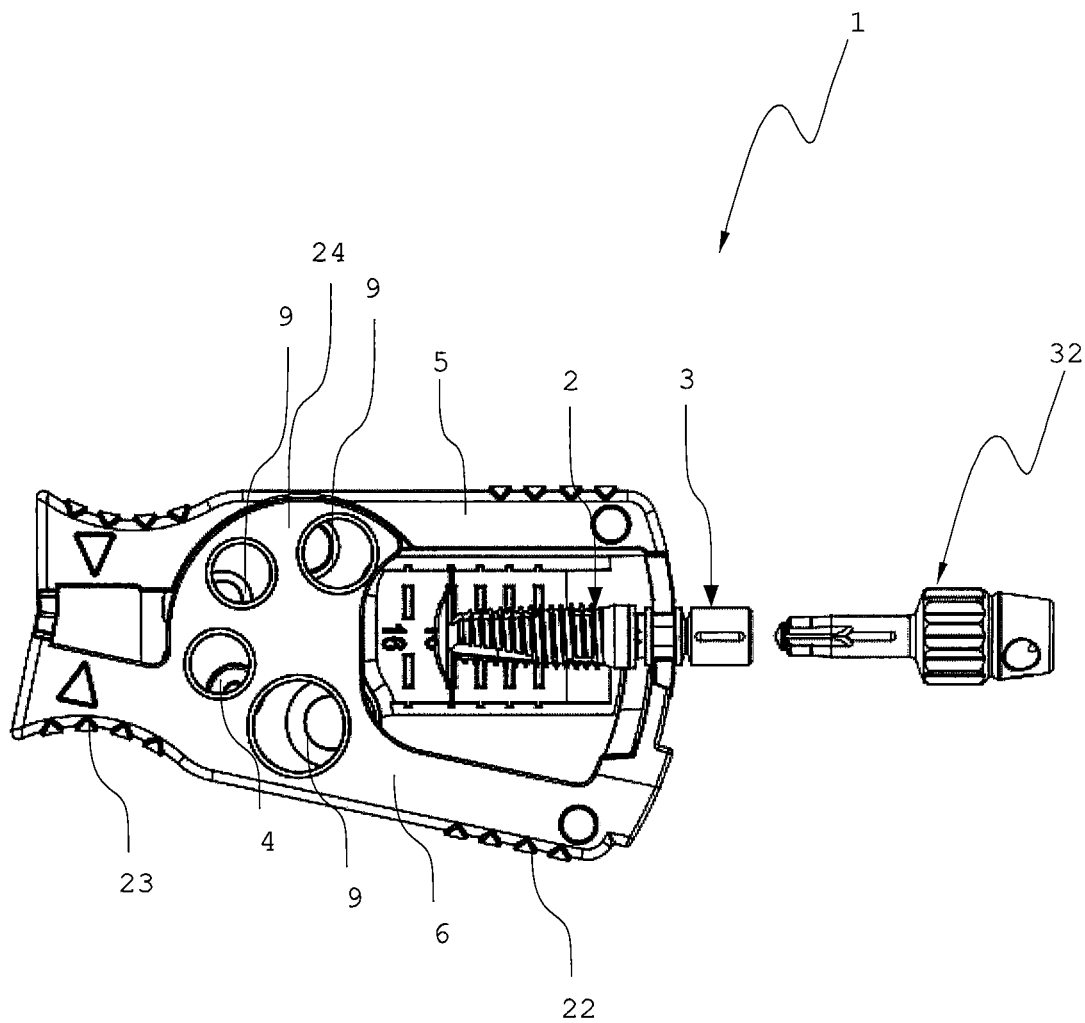
Figure 5:
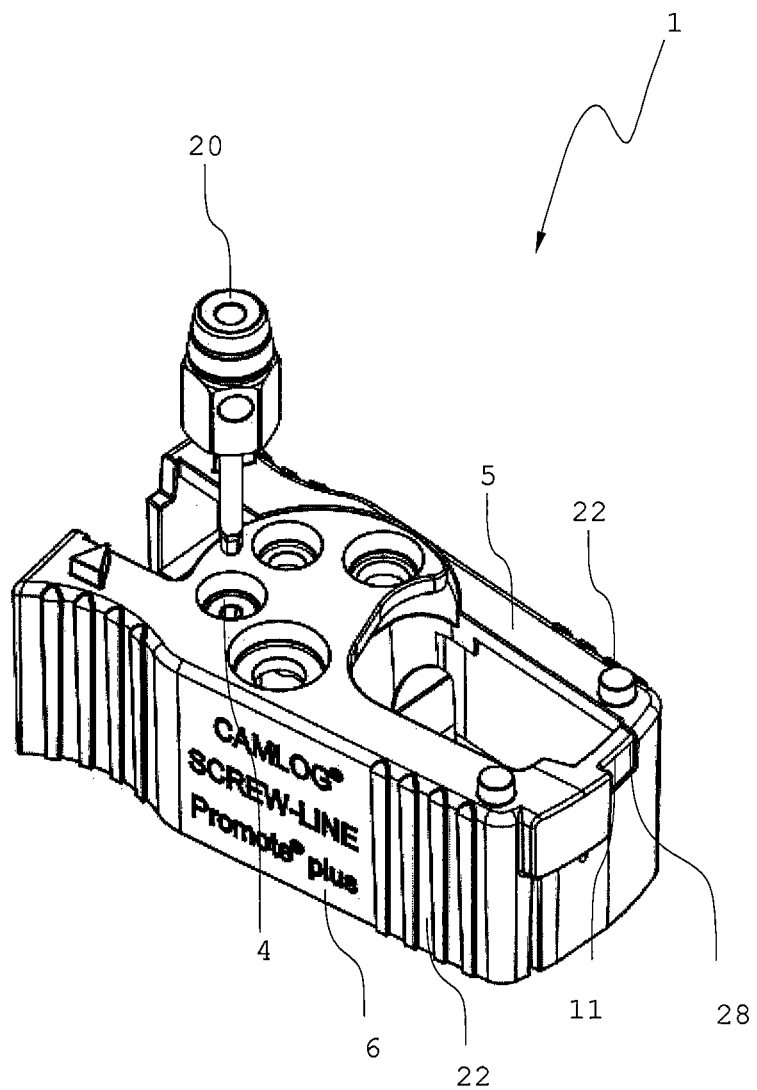
Figure 6:
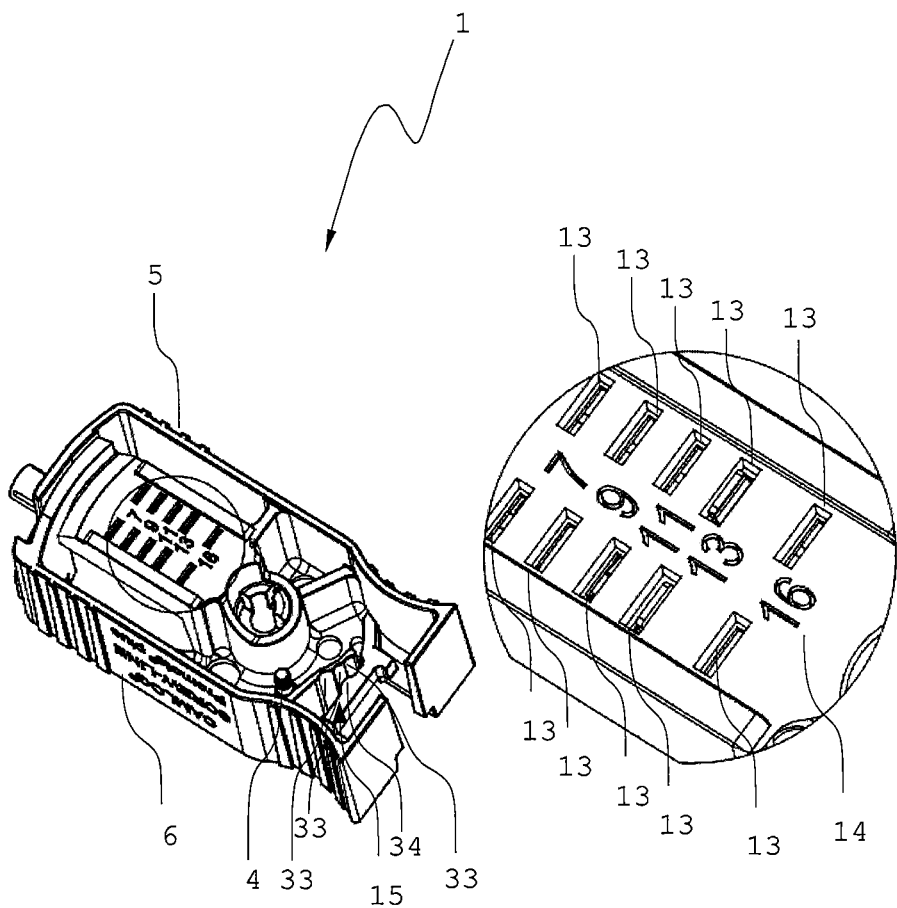
Figure 7:
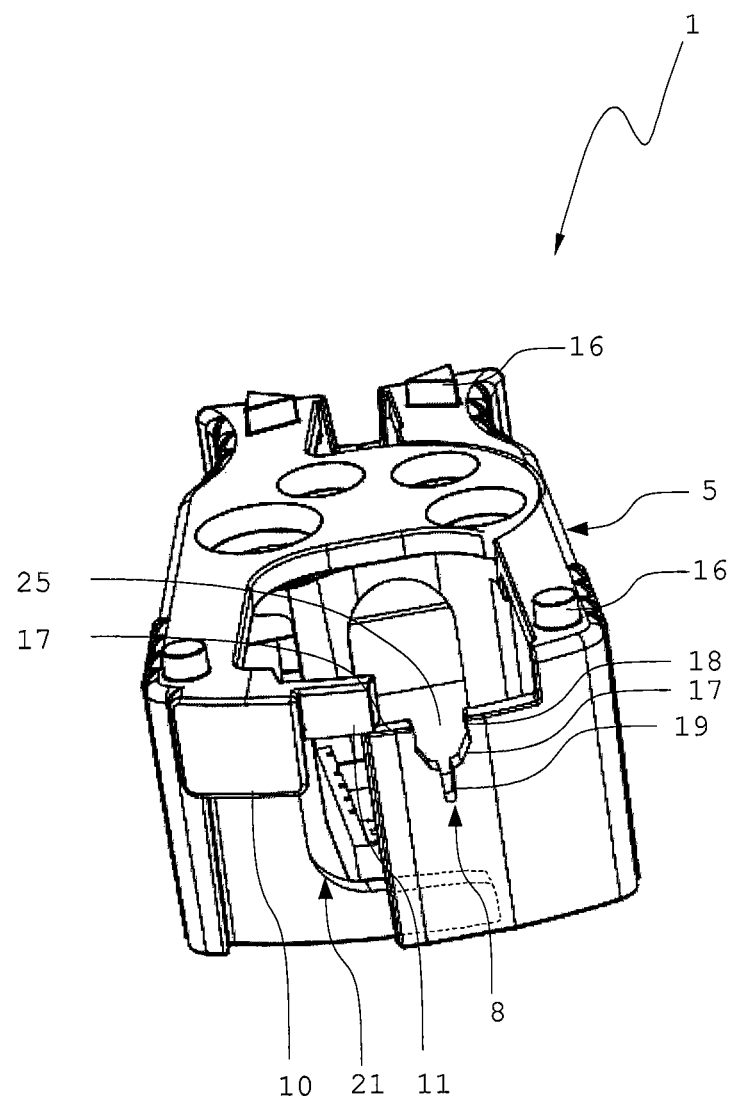
Figure 8:
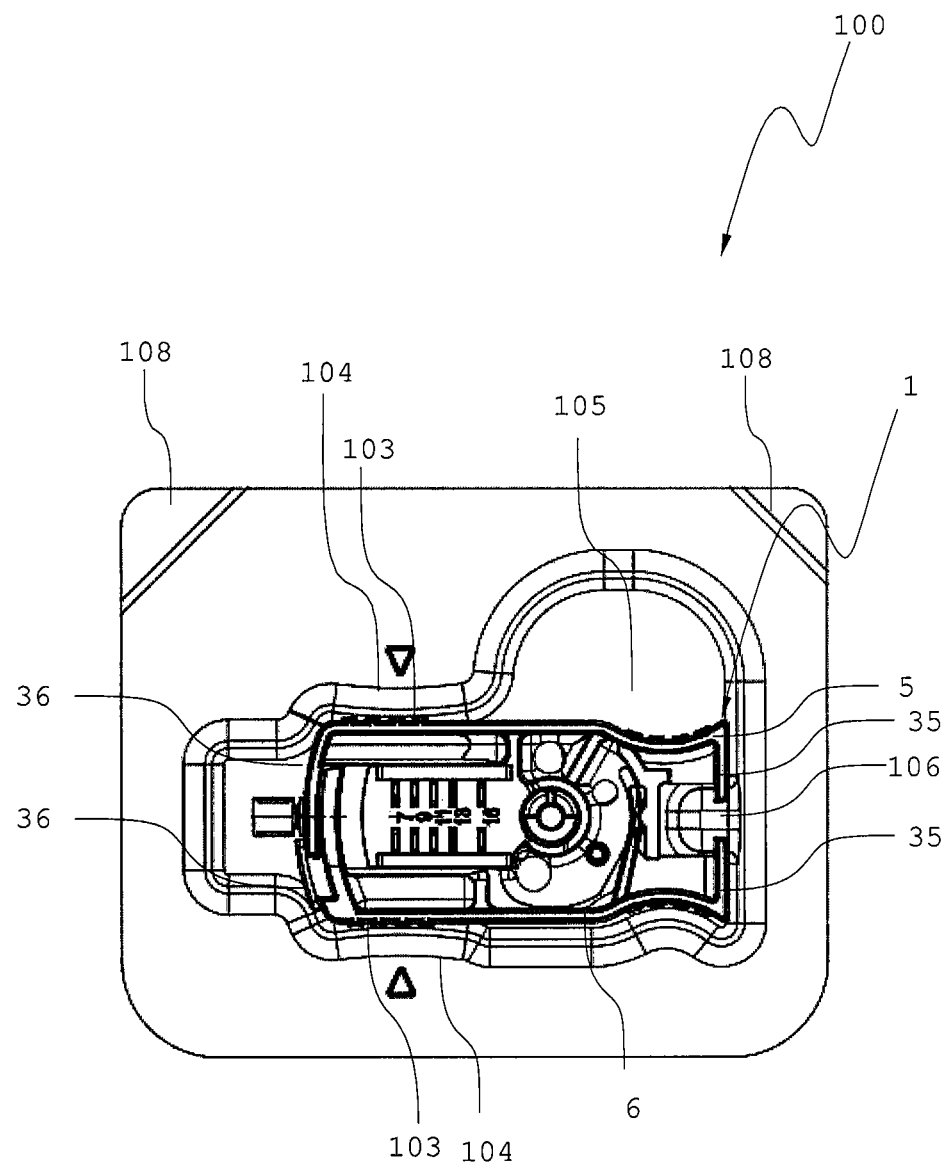
Figure 9:
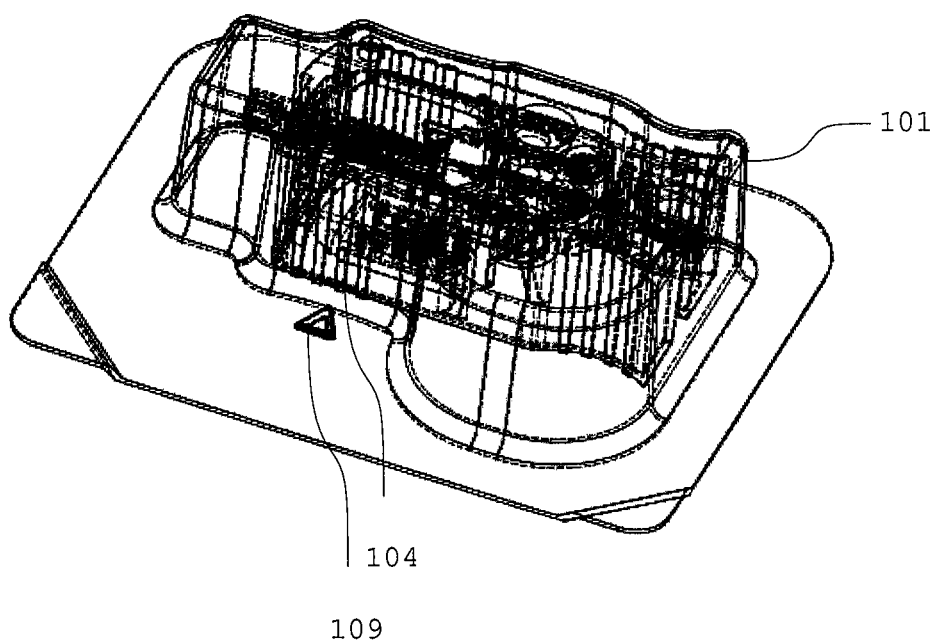
Figure 10:
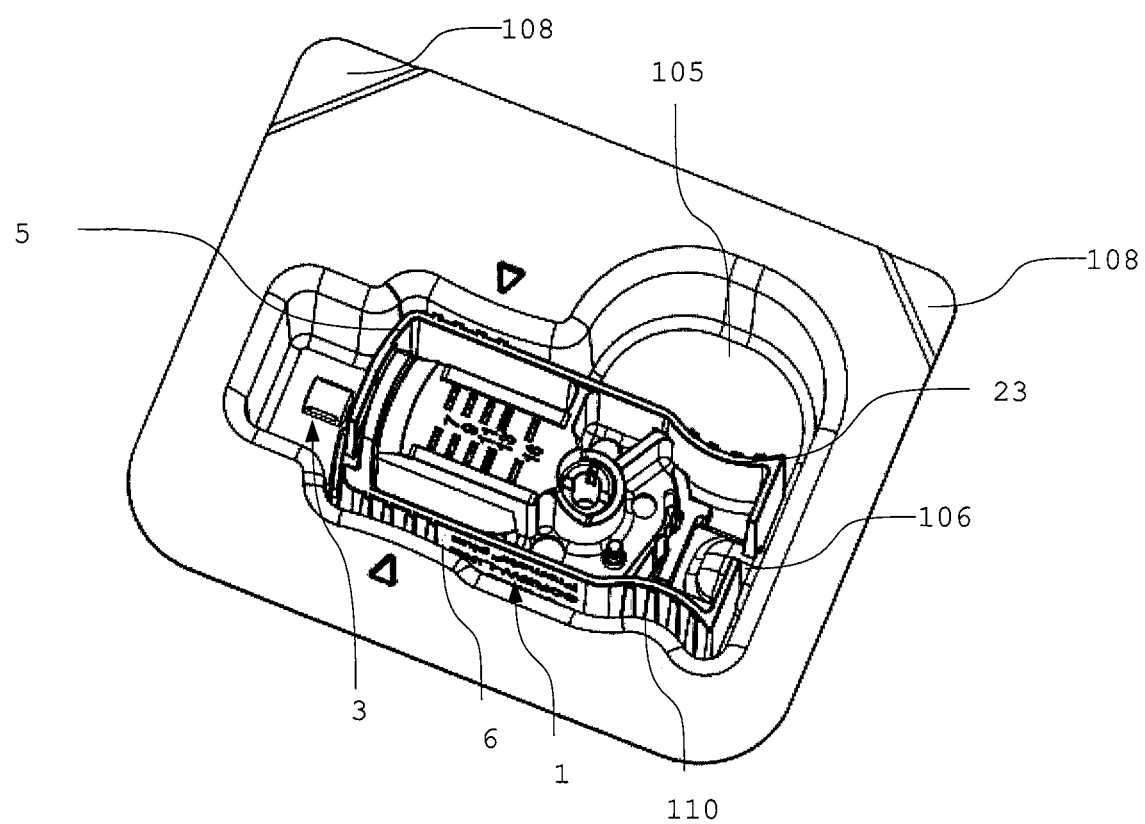
Figure 11A:
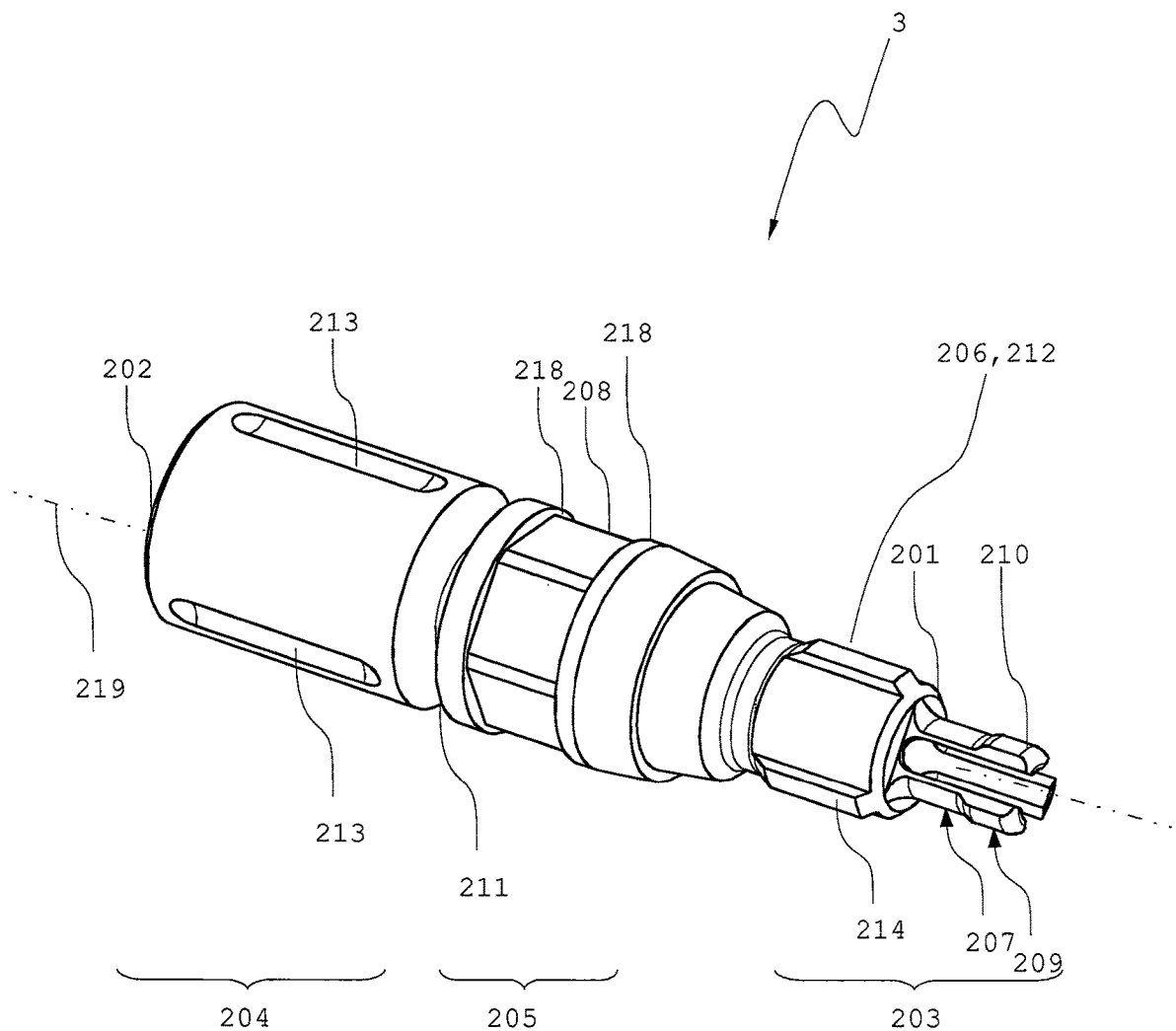
Figure 12:
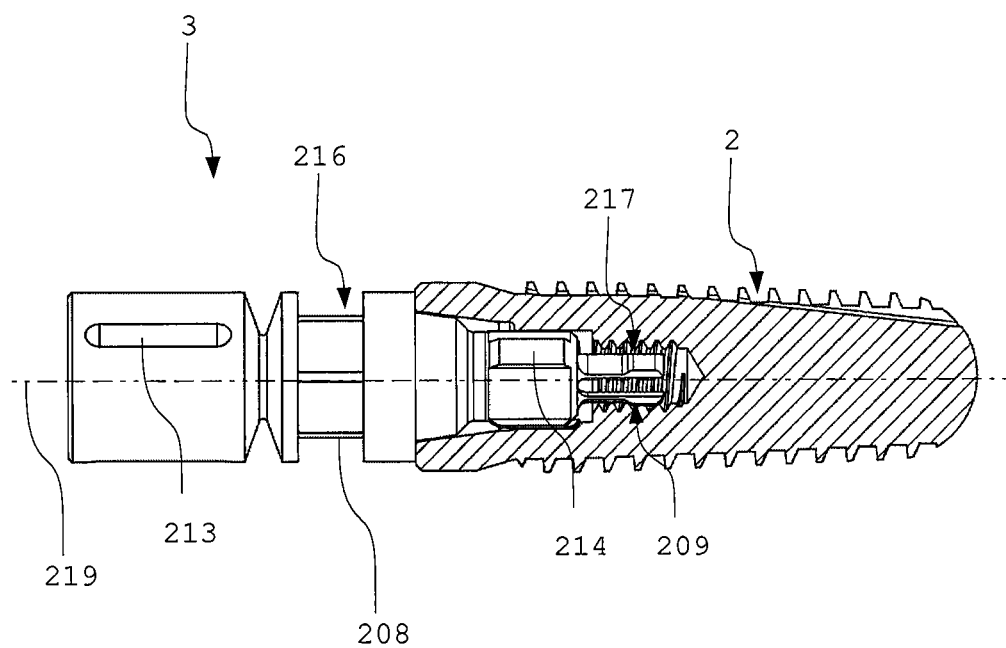
Figure 13:
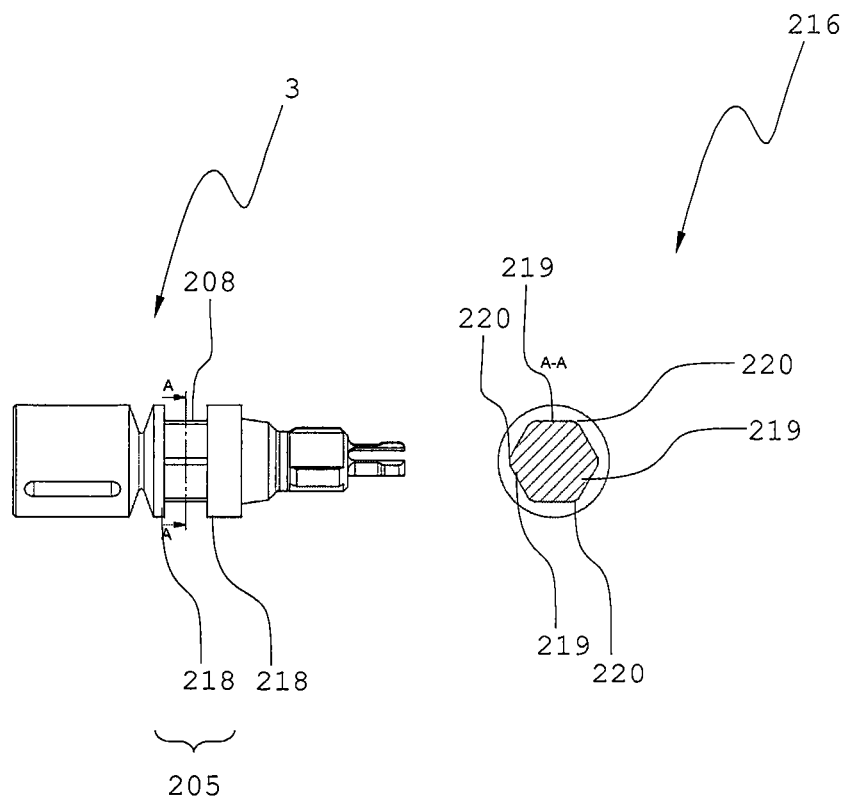
Figure 14:
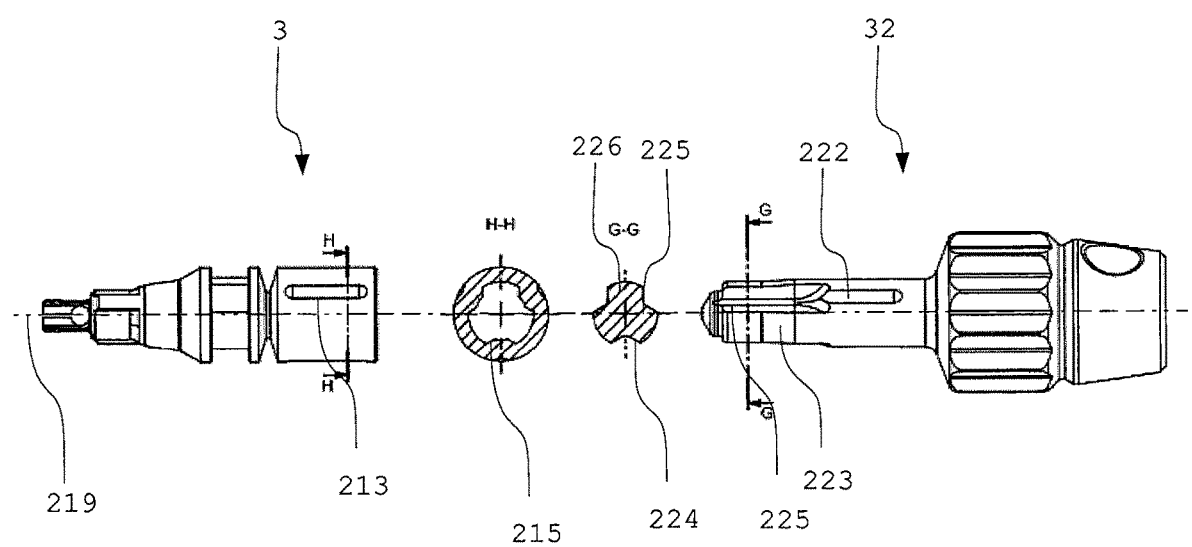
Figure 15:
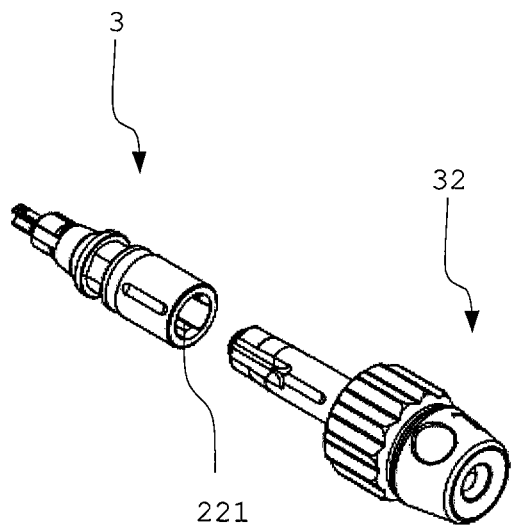

Non-limiting embodiments of the invention are described, by way of example only, with respect to the accompanying drawings, in which:

FIG. 1: is a perspective view of a retainer with an implant, an adapter and an insertion device, FIG. 2: is a top view of a retainer FIG. 3: is a perspective view of a retainer in a first position, FIG. 4: is a top view of a retainer in a second position, FIG. 5: is a perspective view of a retainer in a third position with a screw driver, FIG. 6: is a bottom view of the retainer and a detailed view of holding structures of the retainer, FIG. 7: is a perspective view of a retainer with a support structure, FIG. 8: is a bottom view of a retainer held in a packaging, FIG. 9: is a perspective view of a recess of a packaging, FIG. 10: is another perspective view of a retainer held in a packaging, FIG. 11a/11b: is a perspective view of an adapter for two embodiments of a surgical device, FIG. 12: shows the adapter of FIG. 11a with an implant, FIG. 13: shows a side view and a cross section of a support section of an adapter for connection to a retainer, FIG. 14: shows a side view of an adapter and an insertion device and a cross section of the connection sections of the adapter and the insertion device, FIG. 15: shows a perspective view of an adapter and an insertion device.

In FIG. 1 a retainer 1 which holds an adapter 3 is shown. The adapter 3 is connected to a dental implant 2. A first support structure 8 holds the adapter 3. The adapter is connectable to an insertion tool 32. The retainer comprises two body parts: A first body part 5 and a second body part 6. The first body part 5 comprises secondary support structures 9 in which a screw 4 can be held. The second body part comprises a round plate 24, which prohibits a removal of the screw 4. The first body part 5 and the second body part 6 may be rotated in relation to each other around a pivot axis 7. A user may actuate the first and second body part in a first way by pressing on a first set of grips 23. The first set of grips 23 are located on first ends 35 of the first body part 5 and the second body part 6. During this rotation the first body part 5 pivots in a direction 39 and the second body part 6 pivots in a direction 38. If a user desires to pivot a first body part 5 and the second body part 6 in a second way then a second set of grips 22 may be pressed. A second set of grips are located at second ends 36 of the first body part 5 and the second body part 6. Hence, the first and second body part may be actuated in a "scissor like manner" with grips on both ends of the "scissor". The pivoting motion in the second way is limited by a first limiting portion 10. The first limiting portion 10 contacts the adapter 3 which is held by the first body part 5 and thus forms a first limiting stop. The second body part also comprises locking means 11 realized as a bar.

This bar locks the adapter 3 in the retainer. Then the pivoting motion cannot extend beyond the contact point as long as the adapter 3 is held by the first body part 5. A pivoting motion in the opposite direction is also limited. The first ends 35 of the first body part 5 and the second body part 6 include contact elements 40 (see FIG. 2). If the second or first body part is pivoted in the second way, then the contact elements 40 limit this motion and act as a second limiting stop. Hence, a range is defined within which a pivoting motion can be conducted.

With reference to FIG. 2 a top view of the retainer is shown. In between the first body part 5 and the second body part 6 a stabilizing structure realized as titanium platelet 12 is shown. The titanium platelet 12 is held by a holding structure 13. There are five holding structures 13 in the form of two slots shown in FIG. 2. Depending on the size of the implant the titanium platelet 12 may be inserted into the suitable holding structure 13. The numbers next to the holding structures indicate the length of the implant. The titanium platelet is a stabilizing structure.

Further FIG. 2 shows projections 16 on the sides of the first and second ends 35, 36. The protections are designed such that the retainer may stand on them once placed on a flat surface like a table or tray.

The retainer holds a healing screw 4. This healing screw 4 is held by a secondary support structure 9 of the first body part 5. The second body part 6 includes screw locking means realized as a round plate 24 for the screw 4. In the exemplary embodiments, the first body part 5 includes four secondary support structures 9 for several different sizes of healing screws. During use only one of those holding structures is occupied. The other three remain empty. Hence, one retainer is adjusted to the length of the implant (as described above) and also may hold the suitable healing screw 4. Above the holding structure for the healing screw 4 of the first body part 5 the plate 24 for locking the healing screw 4 in is arranged. In the position shown in FIG. 2 the healing screw is removable from the retainer. In this position holes 42 of the second body part 6 are arranged concentrically with a longitudinal axis of the healing screw. In this position and only in this position the healing screw 4 may be removed.

FIG. 3 shows the first and second body part 5, 6 in a first position. First and second body part 5, 6 can be brought into three different positions. In the first position the screw 4, adapter 32 and the implant 2 are locked in the device and cannot be removed. This position is utilized for transporting and handling the retainer. Once delivered to a surgeon or dentist, the dentist can bring first and second body part 5, 6 into the second position.

FIG. 4 shows the first body part 5 and second body part 6 in the second position. As can be seen from FIG. 4 the holes 42 are not concentrically aligned with the longitudinal axis of healing screw 4 or the secondary support structures 9 of the healing screws. Hence, a healing screw 4 may not be removed from the retainer. The healing screw is fixed inside the retainer and thus cannot be lost. However, the adapter 3 and implant 2 are removable from the retainer in the position shown in FIG. 4. Thus, the surgeon can use an insertion tool 32 to remove the adapter 4 and the implant 2 from the retainer and implant the implant 4. After the implantation the surgeon or dentist may need the healing screw 4. To access the healing screw 4 the retainer 1 is brought into the third position shown in FIG. 5.

FIG. 5 shows a removal of a healing screw 4 with a screw driver 20. If the first body part 5 and a second body part 6 are in the third position (see also FIG. 2) then the healing screw 4 can be attached to a screw driver 20 and the healing screw 4 can be removed from the retainer 1. This position can only be reached if the adapter was previously removed. After removal of the adapter 3 and implant 2, the retainer is pivoted by pressing grips 22 to a third limiting stop. The first and second body part may not pivot past the third limiting stop. The third limiting stop is defined by a second limiting portion 28 of the second body part 6 being in contact with the first body part 5. The third limiting stop also defines the position in which the healing screw 4 is removable from the retainer 1.

FIG. 6 shows a detailed view of the holding structures 13 for the platelet 12. The holding structures 13 are five pairs of holes. The titanium platelet 12 includes a pair of pins (not shown). This pair of pins is inserted into one of the five pairs of holes.

Further FIG. 6 discloses engagement means 15. The engagement means 15 comprise grooves 33 and a ledge 34. The grooves 33 are arranged on the second body part 6. Each of these grooves 33 defines one position into which the first and second body parts are movable. The first body part 5 is in contact with the grooves 33 with a groove ledge 34. The groove ledge 34 is part of an elongated bar attached to the first body part and snaps into the grooves 33. Thereby for each of the three grooves a position in held. If user wants to pivot the first and second body part to another position the grips, either grips 23 for a movement in the first way or grips 22 for a movement in a second way are pressed and the groove ledge 34 jumps to another groove 33.

FIG. 7 shows a perspective view of the retainer 1 on a side with a first support structure 8. In the first support structure 8 the adapter 3 can be held. The first support structure 8 is a part of the first body part 5. The adapter 3 is held in the noncircular shape 17. The shape 17 has a V-form such that a hexagonal section of the adapter 3 can be placed in the flat faces of the shape 17. Further the support structure includes ledges 18 on both sides of an insertion opening. The ledges 18 fix the adapter on the shape 17. The support structure includes a gap 19. The distance between the ledges 18 is shorter than a diameter of the adapter 3. Hence, the ledges have to be pushed outwardly when the adapter is inserted. The gap 19 provides the first support structure 8 with the necessary flexibility.

Once the adapter 3 is loaded into the support section 8, then the first and second body part are pivoted by pressing grips 22 (see FIG. 1) in the second way such that adapter locking means 11 are slid such as to close the insertion opening 25. The adapter 3 may not be removed then because adapter locking means 11 consisting of a short bar close the insertion opening 25.

With reference to FIGS. 8, 9 and 10 a packaging 100 for a retainer 1 is described. The packaging 100 includes two parts: a transparent blister (shown) and a removable cover (not shown). The blister has a recess 101. In the recess 101 the retainer 1 is held. The packaging 100 includes two features which prohibit a pivoting motion of the retainer 1. First the recess 101 is formed such that it includes contact areas 103 on the inner surface of the wall of the recess 101. The contact areas 103 prohibit the motion, in which the ends 36 of the retainer depart from each other. The opposite motion is prohibited by the first limiting stop 10 (see FIG. 1). Further the recess 101 includes a bulge 106. The bulge 106 extends between ends 35 and thus the ends 35 may not be moved towards each other by pressing the grips 23.

When a user desires to remove the retainer 1 from packaging 100, first the removable cover needs to be removed. The removable cover is a peel-off seal. The peel-off grips 108 provide an easy access to the peel-off seal. Afterwards a user may choose either of two options to remove the retainer 1 from the recess 101.

In the first option the user utilizes an area for withdrawal 105. With reference to FIG. 10 the user holds the retainer on the grip 23 of the second body part 6 on both sides of the wall forming the grip. The recess includes an indentation 110 on the grip 23 of the first body part 5. This indentation 110 prevents a user from using both grips 23 to remove the retainer 1 from the recess. This would be undesired since it could trigger a pivoting motion and thus a release of adapter 3 and implant 2.

In the second option the user utilizes outer surfaces for gripping 104 (see FIG. 9). The outer surface for gripping 104 is indicated to a user by a pointer 109. The blister is deformable and therefore gripping both outer surfaces 104 at the same time results in clamping the retainer 1 with the contact areas 103. Then a user may flip the packaging to the position shown in FIG. 9 and place the retainer on a flat surface such as a table or tray. Softening the grip will enable the user to then simply take off the blister.

FIG. 11a shows a schematic view of the adapter 3 in a perspective view. The adapter 3 is intended to connect the implant 2 to the insertion device 32.

The adapter 3 comprises three sections: a surgical section 203, an engagement section 204 and a support section 205. The surgical section 203 is sized according to the size of the according implant 2. The engagement section 204 on the other hand is standardized to a single size such that a dentist only needs one insertion device 32 with one size for all sizes of implants.

The surgical section 203 engages the implant 2 and is located on the side of a first end 201 of the adapter 3. The surgical section 203 comprises force transmission means 206. These force transmission means transfer a torque around a longitudinal axis 219 from the adapter 3 to the dental implant 2. The force transmission mean 206 shown in FIG. 11a is a spline shaft 212. Lobes 214 extend from a circular base. The force transmission means 206 are inserted into a spline hub of the dental implant 2. The spline hub is adapted in size to receive the spline shaft 212.

The surgical section 203 further comprises attachment elements 207. The attachment elements 207 provide a retention force along the longitudinal axis 219 between implant 2 and adapter 3. Hence, the adapter is securely fixed in the implant 2. To remove the adapter 3 from the implant 2 a preset force threshold needs to be overcome. The attachment elements 207 are spring elements 209. The three spring elements 209 seen in FIG. 11a are basically longitudinal bars which extend from the first end 201. These bars may be deflected in a radially inward direction. The resistance to such reflection provides a frictional retention force which prevents an unintended removal of the adapter 3 from the implant 2. Also the retention force enables handling the implant with the adapter. Thus, damage or contamination of the implant can be avoided. The spring elements 209 include each one contact sections 210 pointing in a radially outward direction.

Figure 11B:
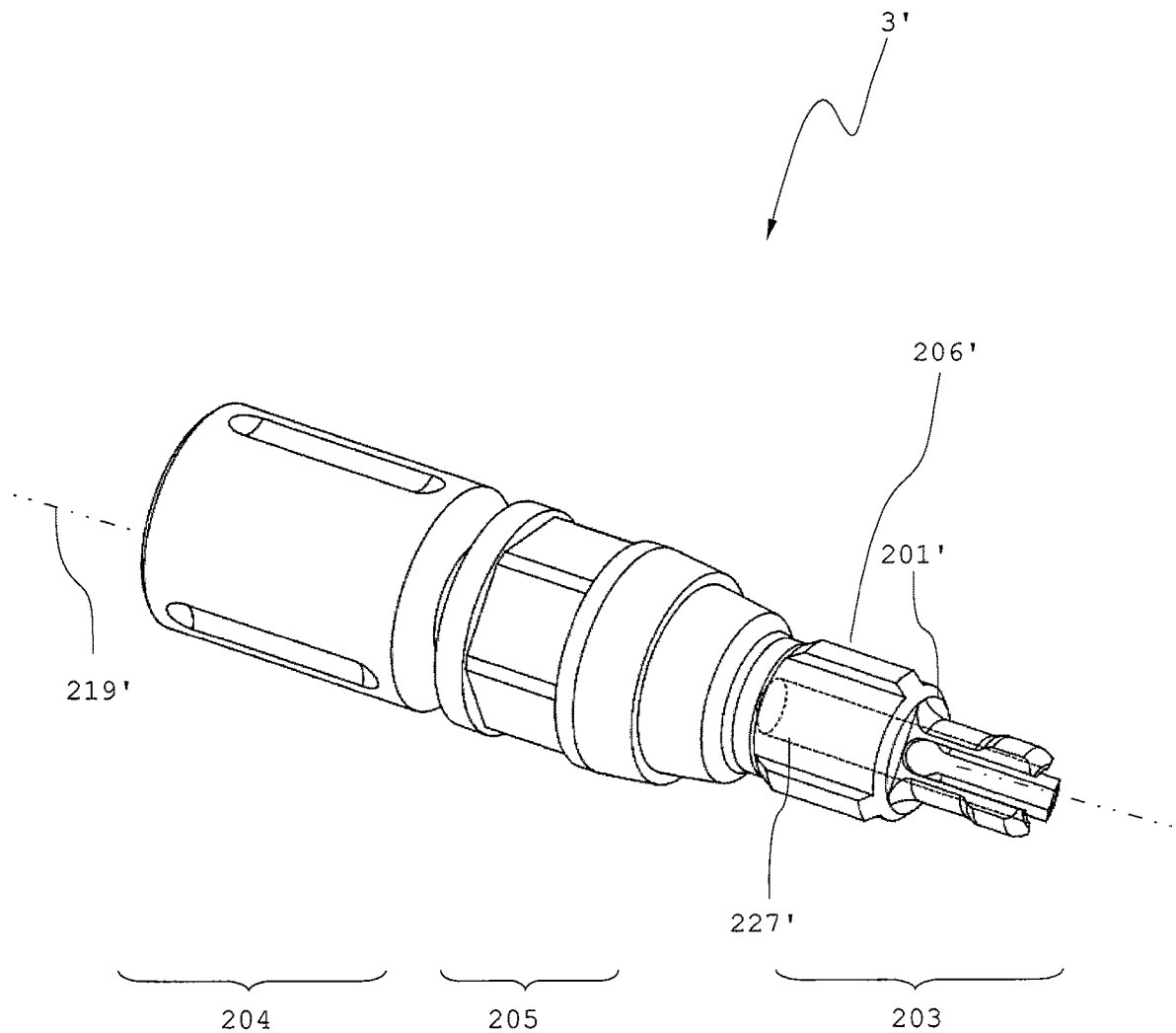

FIG. 11b shows an adapter 3' similar to the one shown in FIG. 11a. However, unlike the adapter in FIG. 11a, a cavity realized as bore 227' extends from the side of the first end 201'. The bore 227' is drilled concentrically and undercuts the force transmission means 206' over their entire length along the longitudinal axis 219'. The bore 227' weakens the resistance of the force transmission means 206' against torsion and allows a twisting of the force transmission means 206'. The diameter of the bore 227' is smaller than an inner diameter of an opening of the attachment members. Thus, during production the bore can be drilled without damaging the attachment members.

As can be seen from FIG. 12, the spring elements 209 engage an inner threading 217 of the implant 2. Ideally the retention force is high enough to allow a stable fixation of the implant 2 and low enough to allow a comfortable removal of the adapter 3 from the implant 2 without any further tools.

It has been found that the retention force of the spring elements may be too high for a comfortable removal with a single larger contact section. In this case two contact sections instead of one could be provided which are spaced apart according to a pitch of the inner treading 217. Thus, the deflection of the spring elements is reduced and a removal is facilitated while the fixation remains stable.

With reference to FIGS. 11a and 11b and 13 the support section 205 is described. The support section comprises two shoulders 218. A recess 208 is located in between the two shoulders 218. Along the recess 208 the adapter 3 has a hexagonal shape 216. A cross section (A-A) of the hexagonal shape 216 shows six flat surfaces 219 (see FIG. 13). As shown in FIG. 13 the flat surfaces are connected via round edges 220.

With reference to FIGS. 11a/11b, 14 and 15 the engagement section 204 is described. The engagement section 204 comprises an opening 221 on the second end 202. A cross-section of this opening is adapted to receive the insertion device 32. The cross-section of the opening 221 is a spline hub 215. The insertion device 32 includes a spline shaft with a corresponding cross-section 224. In between lobes 226 there are depressions 225. The depressions 225 may be connected to a shaft of the insertion 32 device with a conical section 223. The conical section 223 allows a releasable attachment between insertion device 32 and adapter 3.

The insertion device 32 further includes orientation notches 222. The orientation notches 222 are arranged at the circumferential position of the depressions 225. In addition the adapter 3 also includes elongated notches 213. In order to bring the spline hub of the adapter and the spline shaft of the insertion device 32 in connection, the notches 222 and 213 are aligned. Then the spline shaft can be directly inserted into the spline hub without user having to find a correct orientation by try and error.

Furthermore FIG. 11a shows a pre-defined breaking point 211 in between support section 205 and engagement section 204. The insertion device 32 transmits a torque to the adapter 3. The adapter transmits this torque via the force transmission means 206 to the implant 2. The implant 2 is thereby screwed into a bone of the jaw. The implant may be inserted into hard cortical bone and thus a high torque may have to be transmitted from the adapter to the implant. However, excessive torque may damage the implant. In order to prohibit such a case the pre-defined breaking point breaks. Thus the transfer of said excessive torque is prevented.

The invention claimed is:

1. A retainer for holding at least a first surgical device and a second surgical device, comprising:
    first and second body parts,
    wherein the first and second body part are pivotable relative to each other,
    the first body part includes a first support structure for holding the first surgical device,
    the retainer includes at least one secondary support structure for the second surgical device,
    the first and the second body parts of the retainer are pivotable in relation to each other in a pivoting motion to at least three pre-defined positions:
    in a first position, the first and second surgical devices are locked in the retainer,
    in a second position, the first surgical device is removable from the first support structure, but not the second surgical device, and
    in a third position, the second surgical device is removable from the retainer
    wherein the pivoting motion is around a fixed pivot axis,
    and wherein the retainer includes a limiting portion which prevents movement to the third position,
    and the limiting portion is adapted to be unlocked by removing the first surgical device.

2. The retainer according to claim 1, wherein the pivot axis extends substantially perpendicular to longitudinal directions of the first and second body parts.

3. The retainer according to claim 1, wherein the retainer is pivotable from the first position to the second position, in a first direction, and from the second position to the third position, in a second direction opposite to the first direction.

4. The retainer according to claim 1, wherein the retainer is pivotable from the first position to the second position, in a first direction, and from the second position to the third position, also in the first direction.

5. The retainer according to claim 1, wherein the retainer comprises locking means for prohibiting removal of the first surgical device.

6. The retainer according to claim 1, wherein the retainer comprises locking means for prohibiting removal of the second surgical device.

7. The retainer according to claim 1, wherein the retainer comprises at least two secondary support structures for the second surgical device.

8. The retainer according to claim 1, wherein the first surgical device includes an adapter and a dental im plant.

9. The retainer according to claim 1, wherein first and second body parts are made from at least one plastic material.

10. The retainer according to claim 1, wherein the body parts are producible by molding.

11. The retainer according to claim 1, wherein the retainer additionally includes a stabilizing structure, and the stabilizing structure comprises a contact section for contact with the first surgical device.

12. The retainer according to claim 11, wherein the contact section of the stabilizing structure comprises one of metal or ceramic.

13. The retainer according to claim 11, wherein the retainer comprising at least two holding structures for the stabilizing structure, the stabilizing structure is attachable to any one of the at least two holding structures, and each holding structure corresponds to one size of the first surgical device.

14. The retainer according to claim 13, wherein the retainer comprises a labeling for the at least two holding structures indicating a corresponding size of the first surgical device.

15. The retainer according to claim 1, wherein the retainer comprises engagement means for defining at least one of the first, second and third positions.

16. The retainer according to claim 1, wherein the retainer includes at least one projection for support on a flat surface.

17. The retainer according to claim 1, the first support structure:
being adapted to hold the first surgical device at a support section for connecting to the first support structure, and the first support structure has an at least partially non-circular shape.

18. The retainer according to claim 1, wherein of the first support structure partially envelops the first surgical device.

19. The retainer according to claim 17, wherein the first support structure is V-shaped for receiving a polygonal cross-section.

20. The retainer according to claim 1, wherein the first support structure comprises projections for removably securing the first surgical device.

21. The retainer according to claim 1, wherein the first support structure comprises a gap for flexibly expanding at least a part of the first support structure.

22. The retainer according to claim 1, wherein the retainer comprises
the first and the second body parts,
the first and second body parts are pivotable relative to each other, and
at least one of the first and second support structure comprises at least one limiting stop for limiting pivoting motion of either of the first and second body parts.

\* \* \* \* \*